(12) United States Patent
Roser (10) Patent No.: US 6,808,507 B2
(45) Date of Patent: Oct. 26, 2004

(54) SAFETY INJECTORS

(75) Inventor: Bruce J. Roser, Cambridge (GB)

(73) Assignee: Cambridge Biostability Ltd., Cambridge (GB)

( * ) Notice: Subject to any disclaimer, the term of this patent is extended or adjusted under 35 U.S.C. 154(b) by 2 days.

(21) Appl. No.: 10/141,968

(22) Filed: May 10, 2002

(65) Prior Publication Data

US 2003/0212362 A1 Nov. 13, 2003

(51) Int. Cl.$^7$ ............................................... A61M 5/00
(52) U.S. Cl. ..................................... 604/110; 604/198
(58) Field of Search .............................. 604/110, 195, 604/198, 218, 232, 263, 207, 208, 210, 212, 197, 192, 187; 206/364, 365, 367

(56) References Cited

U.S. PATENT DOCUMENTS

| | | | |
|---|---|---|---|
| 4,013,073 A | * 3/1977 | Cunningham | 604/204 |
| 4,018,222 A | * 4/1977 | McAleer et al. | 604/113 |
| 5,782,804 A | 7/1998 | McMahon | 604/110 |
| 5,980,488 A | 11/1999 | Thorne | 604/110 |
| 6,015,438 A | 1/2000 | Shaw | 624/195 |
| 6,050,977 A | 4/2000 | Adams | 604/195 |
| 6,102,896 A | 8/2000 | Roser | 604/218 |
| 6,224,567 B1 | 5/2001 | Roser | 604/68 |

OTHER PUBLICATIONS http://www.devicelink.com/expo/awards02/EMDM.html "Medical Design Excellence Awards"Note p. 2, BD UniJect Prefill Injection Device.*
Jodar et al, Genetic Engineering News, Feb. 15, 1998, pp. 1–5, Revolutionizing Immunizations.
Kane et al, Bulletin of the World Health Org, 77 (10), pp. 801–807, 1999, Transmission of hepatitis B, hepatitis C and . . . .

* cited by examiner

*Primary Examiner*—Anhtuan T. Nguyen
(74) *Attorney, Agent, or Firm*—Jacobson Holman PLLC (57) ABSTRACT

A simple mechanism that provides the manipulations required to deliver a correct injection and also incorporates the safety modifications that are needed to prevent needle-stick injury and ensure self destruct capability. A surprisingly simple and cheap modification to a sterile package for the standard syringe and needle can successfully be used to automate the medical skills needed to deliver a safe injection and dispose of the hazardous needle afterwards. The sterile package consists of a housing for the syringe barrel, which can telescope into a larger diameter hollow cap covering the syringe plunger. The syringe and needle are located fully inside this two-part packaging sheath, which completely encloses and protects them.

19 Claims, 7 Drawing Sheets

SAFETY INJECTORS

FIELD OF THE INVENTION

The present invention relates to the field of injecting predetermined doses of medication without a patient seeing a needle before, during or after an injection.

BACKGROUND OF THE INVENTION

The conventional syringe and needle that are used to give injections are dangerous. Over 8,000 cases of hepatitis B are caused every year by needlestick injuries in the United States. The HIV virus and hepatitis C are also often transmitted by this route.

The situation has become so severe that the United States Congress passed the Needlestick Safety and Prevention Act, which became law in November, 2000, prohibiting injections except by means of safety syringes which prevent contact with the needle after use. However injections using a safety syringe are still cumbersome and painful and the needle is exposed and dangerous before the injection is given.

AIDS, Hepatitis B and Hepatitis C are much more prevalent as result of unsafe injection practices in the developing world. It is estimated that 8–16 million cases of Hepatitis B, 2.3–4.7 million cases of Hepatitis C and 80,000–160,000 HIV infections occur each year as a direct result of unsafe injections (A. Kane, J. Lloyd, M. Zaffran, L. Simonsen, and M. Kane, Transmission of hepatitis B, hepatitis C and human immunodeficiency viruses through unsafe injections in the developing world: model-based regional estimates. *Bull. World Health Org.* 77, 801–807 (1999). This is a problem that urgently requires a safe and cost-effective solution.

With most drug formulations, the approved process of giving a subcutaneous or intramuscular injection with a needle and syringe involves performing the following steps, all of which require sterile technique:

1. Take the freeze-dried drug, in its rubber-capped glass vial, from the refrigerator and open the sterile cap.
2. Take a vial of sterile water for injection (WFI) from its box.
3. Remove a wide-bore needle from its sterile packaging.
4. Remove a sterile disposable syringe from its sterile packaging.
5. Attach the needle to the syringe.
6. Use the syringe to aspirate the correct volume of sterile WFI.
7. Deliver this WFI into the vial containing the freeze-dried drug.
8. Swirl or gently shake the vial, without foaming, until the drug is completely dissolved.
9. Aspirate the required dose back into the syringe.
10. Remove a narrow bore needle from its sterile packaging.
11. Replace the used wide bore needle with the fresh narrow bore needle for injection.
12. Expel all the air from the syringe and needle.
13. Carefully swab the skin over the injection site with disinfectant.
14. Insert the needle to the correct depth and location with minimal pain.
15. Inject the drug and withdraw the needle.
16. Permanently dispose of the needles and syringe to prevent needlestick injury to the operator or third parties.

These techniques must be taught to health care professionals. This is not a suitable process for the untrained layman.

The World Health Organization has estimated that it will need to deliver 3.6 billion injections per year by 2005 and that it will not be able to access the medically trained staff to achieve this goal. This old fashioned technology has therefore been deemed by the World Health Organization (WHO) to be incompatible with their requirements for planned Global Program of Vaccination and Immunization (GPV) initiatives. The WHO has formally called for a program of research and development to develop radical new technology for vaccine delivery. (L. Jodar, T. Aguado, J. Lloyd, and P-H Lambert (1998), Revolutionizing Immunizations, *Gen. Eng. News* 18 (P. 6).

The functional criteria required by the WHO are:

Injection device and vaccine dose packaged together;
Safe disposal of contaminated needles and other material;
Zero risk of cross infection;
No waste;
No pain; and
Affordable.

Another hazard of syringes is their re-use; often after inadequate washing and sterilizing, especially in the developing world. These re-used syringes have also caused serious outbreaks of infection. This problem requires "self-destruct" or "single-use" syringes that automatically disable themselves after their first use.

The industry has addressed these challenges by a complete redesign of the needle and syringe to incorporate automatic or semi-automatic covering of the needle after use (U.S. Pat. No. 5,980,488) or retraction of the needle by rubber bands, springs or vacuum into the body of the syringe (U.S. Pat. Nos. 5,782,804; 6,015,438; 6,050,977) or modifications that destroy the functionality of the syringe mechanism after one use (Becton Dickinson "Soloshot™" syringes). These so-called safety syringes are inevitably much more expensive than the standard syringe which retails at around $0.03–0.07 per unit. Many of the new safety syringes cost $0.50 to $1.00 each. These devices are not yet universally used in mass vaccination campaigns because the increase in expense cannot be supported by the agencies involved.

An inexpensive, single-use, self-destruct, pre-filled device recently introduced is the "Uniject™" made by Becton Dickinson and Company. This plastic blister with attached needle is certainly cheap but it still requires training and skill to use and has a dangerous exposed needle, which can cause needlestick injury both before and after the injection.

A series of novel solutions to these problems in the form of a family of disposable injector devices that operate on principles different from the standard syringe and needle is described in U.S. Pat. No. 6,102,896. Essentially these devices, along with most others that have been described, involve redesigns of the technology of injection to eliminate the hazards and simplify the skills needed so that training is no longer required.

Some of the devices described in the '896 patent actually incorporate similar principles to the conventional syringe and hollow metal needle as well as features to simplify and automate the steps of injection. This approach will only be successful if the new devices can demonstrate the remarkable durability and robustness of design that has enabled the syringe and needle to totally dominate the field for over 150 years without any fundamental changes.

Additionally, some of the elements of design in the devices described in '896 patent require very precise manufacturing and quality control to ensure that a sequence of steps required for their operation proceed in the required order. These considerations make these devices less than ideal. A more attractive solution would be a robust and easily manufactured device that has the elegant simplicity of the syringe and needle plus the benefits of automation and safety now required by law.

SUMMARY OF THE INVENTION

A novel approach is to actually retain the existing well-proven devices such as the syringe and needle or the Uniject™ as the core drug delivery device but to add to them a simple mechanism that provides the manipulations required to deliver a correct injection and also incorporates the safety modifications that are needed to prevent needle-stick injury and ensure self destruct capability. A surprisingly simple and cheap modification to a sterile package for the standard syringe and needle can successfully be used to automate the medical skills needed to deliver a safe injection and dispose of the hazardous needle afterwards. The sterile package consists of a housing for the syringe barrel, which can telescope into a larger diameter hollow cap covering the syringe plunger. The syringe and needle are located fully inside this two-part packaging sheath, which completely encloses and protects them.

Accordingly, it is an object of the present invention to provide an injection of a predetermined dose of medication without a patient seeing a needle before, during or after an injection.

It is another object of the present invention to provide a sterile package consisting of a housing for a syringe barrel, which can telescope into a larger diameter hollow cap covering a syringe plunger with a syringe and needle located fully inside the syringe barrel and hollow cap to completely enclose the syringe after use.

It is yet another object of the present invention to provide two plastic injection molding parts and a spring which are used in combination with a pre-filled syringe to inject an individual and completely conceal a used syringe.

It is still yet another object of the present invention to use a pre-filled blister-type injection device for injection of a predetermined amount of medication and have the injection needle sealed between a barrel and a cap for safe disposal.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 4A(1) is a sectional view showing the mounting of the distal free end of the safety injection device pressed against the skin of the patient.

FIG. 4A(2) is a longitudinal sectional view shifted 90 degrees with respect to FIG. 4A(1).

FIG. 4B(1) shows the initial downward movement of the cap to compress the spring and move the needle into the skin of the patient.

FIG. 4B(2) is a longitudinal sectional view shifted 90 degrees with respect to FIG. 4B(1).

FIG. 4C(1) illustrates the continued downward movement of the cap and the compression of the collar of the syringe inside the hollow hub of the syringe.

FIG. 4C(2) is a longitudinal sectional view shifted 90 degrees with respect to FIG. 4C(1).

FIG. 4D(1) illustrates continued downward movement of the cap to force medication from the blister into the subcutaneous tissues of the patient and the surrounding of the blister by the shaped plastic molding.

FIG. 4D(2) is a longitudinal sectional view shifted 90 degrees with respect to FIG. 4D(1).

FIG. 4E(1) illustrates the release of downward pressure on the blister injector so that the bias of the return spring causes the blister injector to move upward into the cap as the final downward movement of the cap causes a cap lock ring to engage a barrel lock ring to house the used syringe.

FIG. 4E(2) is a longitudinal sectional view shifted 90 degrees with respect to FIG. 4E(1).

DETAILED DESCRIPTION OF THE PREFERRED EMBODIMENTS

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 1A:
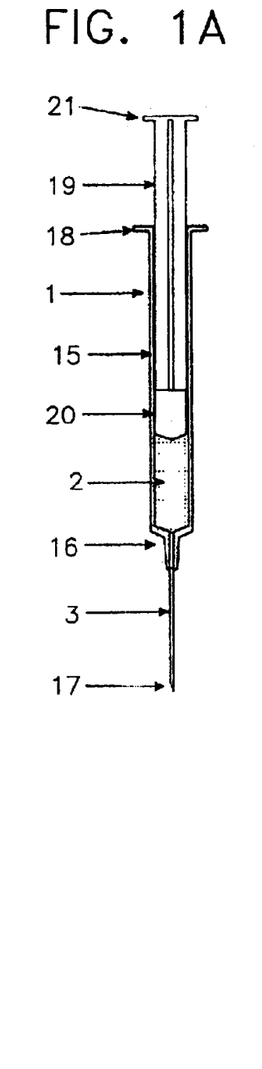
FIG. 1A illustrates a conventional pre-filled syringe.
Figures 1B, 1C:
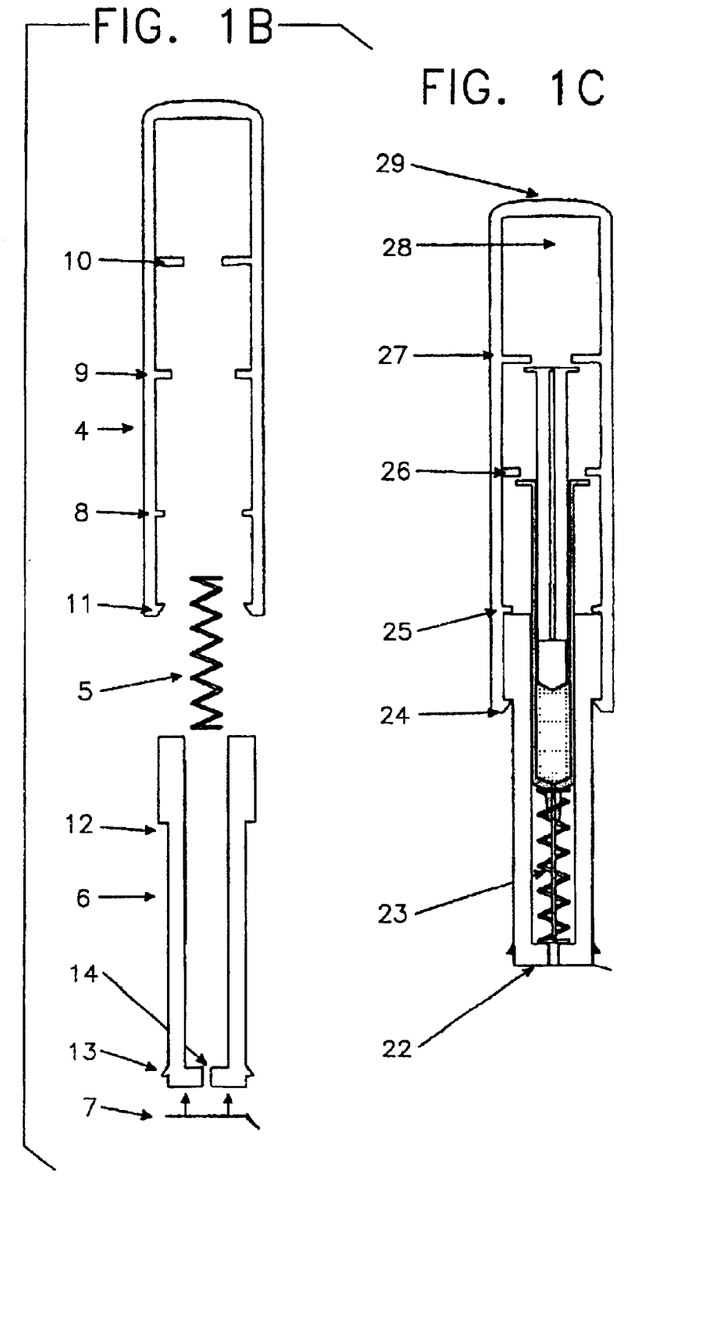
FIG. 1B is an exploded view of the safety injector according to the present invention illustrating a cylindrical cap, a cylindrical barrel housing and spring.
FIG. 1C is a sectional view of a syringe of FIG. 1A mounted in the assembled parts of FIG. 1B.

FIG. 1B shows the device of the present invention in an exploded view and in an assembled view (FIG. 1C) incorporating a pre-filled syringe as shown in FIG. 1A. A conventional pre-filled syringe (1) such as the Hypak™ (Becton Dickinson and Company) or a similar syringe, contains the dose of drug or vaccine (2) and has an attached needle (3). The syringe is to be housed in a cylindrical cap (4) and is located on a spring (5) which lies in the lumen of a cylindrical barrel housing (6), the free end of which is protected by an adhesive foil (7) having a pull tab at one end.

The cap (4) has, on its inside surface, three sets of different sized break-tabs (8, 9 and 10) and a ramp shaped locking ring (11) which, during assembly, locks over the distal end of the wider part of the barrel housing (12) and, after use, locks over a matching ramp shaped locking ring (13) on the barrel housing (6) to lock and disable the used device. After manufacture, assembly and sterilization, sterility is maintained in the device by sealing the needle orifice (14) in the barrel housing (6) with the adhesive foil (7) made of an adhesive transfer tape such as the Adhesives Research Ltd., type ARcare 7396 CO# H2923 or similar adhesive tape.

The barrel (15) of the syringe (1) has a hub end (16) into which the blunt end of a stainless steel hollow needle (3) is fused. The opposite end of the needle is sharpened in the conventional way to a needle point (17).

The other end of the barrel (15) carries an expanded flange (18). The plunger (19), which is located inside the barrel (15), has an elastomeric stopper (20) at one end, which is in a sliding seal in the barrel (15) and, at the other end, a flange (21) which is smaller in diameter than the barrel flange (18).

For assembly, the free end (22) of the barrel housing (6) is first closed off by applying the adhesive transfer foil (7). The spring (5) is inserted into the lumen (23) of the barrel housing (6) in which it is in a loose sliding fit. Because the barrel (15) of the syringe (1) is in a sliding fit in the barrel housing (6), the syringe is held in a coaxial orientation with respect to the barrel housing thus facilitating the attachment of the cap (4) in the correct position.

The cap (4) is slid over the barrel housing until the locking ring (11) seats into the recess (24) of the barrel housing (6) and simultaneously, the first snap tabs (8) come to rest on the wide top (25) of the barrel housing (6). This locks the cap (4) in place on the barrel housing (6) producing a closed and protective environment for the syringe, needle and contents. In this storage position, the second set of break tabs (9) is in register with and just above (26) the barrel flange (18) and the third set of break tabs (10) is in register with and just above (27) the plunger flange (21). Above the third set of break tabs (10) there is a free space (28), which will eventually house the flange (21) end of the syringe (1) when the device has been used.

Figure 2A:
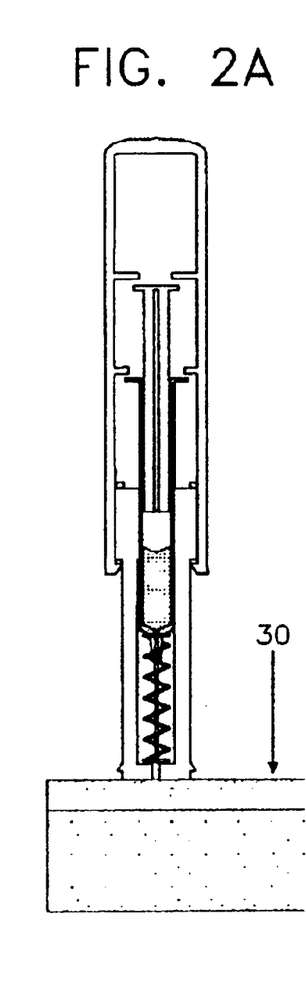
FIG. 2A illustrates the safety injector of the present invention positioned against a patient's skin.

In use, the adhesive transfer foil (7) is removed which transfers a layer of skin adhesive from the adhesive transfer foil (7) to the free end (22) of the barrel housing (6). This adhesive coated end (22) of the device is held against the patient's skin (30) (FIG. 2A) at the injection site by the operator pressing on the free end (29) of the cap (4). The adhesive prevents accidental slippage of the device as increasing pressure is applied to the free end (29) of the cap (4) until the first set of break tabs (8) suddenly give way causing the cap (4) to telescope over and around the barrel housing (6).

Figure 2B:
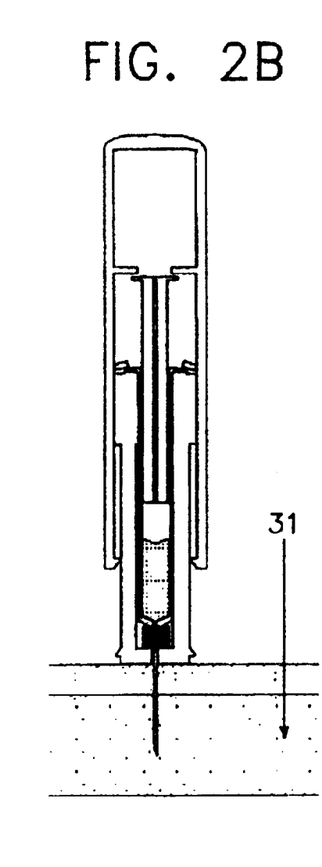
FIG. 2B illustrates a partial compression of the cylindrical cap towards the cylindrical barrel housing for injection of a patient with a syringe.

This causes the second set of break tabs (9) to engage with the barrel flange (18) and drive the syringe barrel towards the free end (22) of the housing (6) thus compressing the spring (5) between the hub end (16) of the barrel (15) and the orifice (14) end of the lumen (23) of the barrel housing (6). This action causes the needle (3) to emerge through the orifice (14) and penetrate to the subcutaneous tissues (31) of the patient (FIG. 2B) until the spring (5) is fully compressed and the syringe (1) bottoms out in the barrel housing (6). Since both the length of the needle (3) and the thickness of the free end (22) of the barrel housing (6) are variable, the depth of needle penetration is factory pre-set.

Figure 2C:
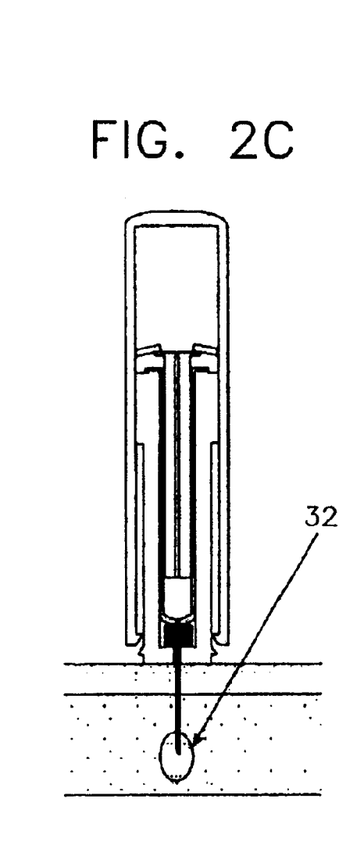
FIG. 2C illustrates the continued movement of the cap towards the barrel housing for dispensing of medication through the syringe into the subcutaneous tissues of a patient.
Figure 2D:
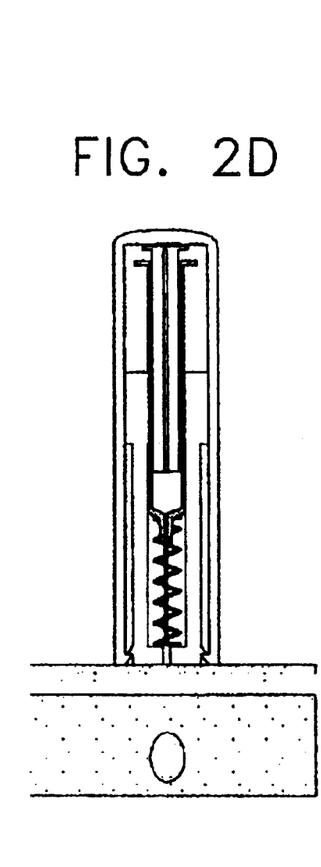
FIG. 2D shows the final positioning of the cap interlocked with the barrel housing to form a disposal container for a used syringe.

When the syringe bottoms out by the complete compression of the spring 5, the sudden increase in pressure of the barrel flange (18) on the second set of break tabs (9) causes the break tabs (9) to give way thus allowing the third set of break tabs (10) to engage the flange (21) on the plunger (19). The continuation of the downward telescopic movement of the cap (4) over the barrel housing (6) then causes the plunger (19) to push the elastomeric stopper (20) towards the hub end (16) of the barrel (15). The friction between the elastomeric stopper (20) and the barrel (15) ensures that downward pressure continues on the barrel and maintains pressure on the spring (5) keeping it fully compressed. The downward movement of the stopper (20) in the barrel (15) causes the discharge of the dose of medicament (2) through the needle (3) and into the subcutaneous tissues (31) until the plunger (19) also bottoms out in the barrel (15) discharging the drug (2) at location (32) (FIG. 2C). This causes an increase in the pressure of the plunger flange (21) on the third set of break tabs (10) causing them to yield. When this happens all downward force on the syringe (1) ceases and the compressed spring (5) causes the syringe (1) to be forced into the free end (29) of the cap (4) thus withdrawing the needle from the tissues (FIG. 2D).

In practice, the high speed of the retraction of the syringe causes the plunger flange to strike the underside of the free end (29) of the cap giving the operator a tactile and audible signal that the syringe has safely withdrawn the needle from the tissues. The final small additional telescopic movement of the cap (4) over the barrel housing (6) engages the lock ring (11) of the cap (4) with the lock ring (13) of the barrel housing (6) thus sealing the used syringe and needle in the device in a safe manner. If the cap (4) is made of transparent or translucent material the safe withdrawal of the needle can be confirmed visually before the adhesive-coated free end (22) of the device is peeled from the patient's skin (30).

Because of this design and method of action, the patient does not see a needle before, during or after the injection. Indeed, if the barrel housing (6) is made from an opaque plastic the patient need not even know that a needle is involved. From the patient's point of view the device would appear identical to a liquid jet injector such as described in U.S. Pat. No. 6,102,896 and in U.S. Pat. No. 6,224,567. As well as protecting the needle from damage or contamination and the operator from needlestick injury, its concealment reduces anxiety, and therefore perceived pain, in nervous patients. Of equal importance from the patient's point of view, the snap-tab mechanism ensures that the needle is thrust through the skin very rapidly thus further reducing pain. Because this design ensures precise axial forces on the needle, which is supported by the surrounding sheath, it also enables the use of needles of smaller outside diameter and wall thickness, thus further reducing trauma and the consequent pain of injection. For these reasons the device is virtually painless in operation.

In its simplest form the device consists only of three parts, two of which can be inexpensive plastic injection-mouldings and the third a simple spring, which can be coiled metal, elastomer or a gas spring. The plastics used have only minor structural requirements and do not need to be expensive "engineering" plastics. The total additional cost of the vaccinator will probably not exceed the original cost of the syringe and needle itself. Thus this device can achieve all of the requirements of safety in injection technology for a modest doubling of the total device cost to around six to ten cents. This should be compared with the $0.20 to $1.50 costs of competitive safety injectors. Unlike other "safety syringes" which require expert handling, the action of the present invention is automatic and the injection depth and the dose are predetermined in the factory making it suitable for use by minimally trained or even untrained personnel.

It is of course possible to use the same principles of automating the function of a syringe and needle described above, to convert other injection devices such as the plastic blister Uniject™ into a safe, comfortable auto injector for subcutaneous or intramuscular delivery. Again, the advantages of this approach are that the needle is enclosed before, during and after the injection; the whole process of injection is fully automated and the cost of the final device is very modest. The design of such a device is illustrated in FIGS. 3A through 3F and its mode of action in FIGS. 4A through 4E. The additional element in the design is a folded, shaped plastic moulding which holds the pre-filled Uniject™ in place in the sheath and which transfers pressure to empty the plastic blister containing the dose at the correct point in the injection cycle.

Figure 3A:
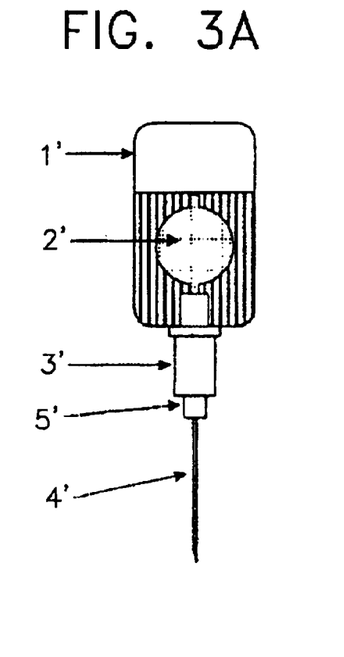
FIG. 3A is a side view of a pre-filled Uniject™ syringe including a plastic blister containing a dose of medication.

The Uniject™ device shown in FIG. 3A is made from two layers of plastic film (1') in which dome shaped depressions are vacuum-formed and which are fused together with the depressions in register so as to form a lenticular cavity; the blister (2'), which is filled with the dose of medicament. Additionally sealed to the film is a hollow hub (3'), which is separated off internally from the dose of medicament in the blister by a thin wall of plastic. A needle (4'), which is sharpened at both ends, is accommodated in the hub by means of a plastic collar (5') firmly attached to it near one end; the hub end. The collar (5') is a snug, sliding fit in the hollow hub (3') and can be moved therein to drive the needle towards the blister thus causing the sharp hub-end of the needle to perforate the thin wall of plastic. This penetrates the seal of the blister so that the dose of medicament is able to flow through the needle when it is expelled by pressure on the blister.

Figure 3B:
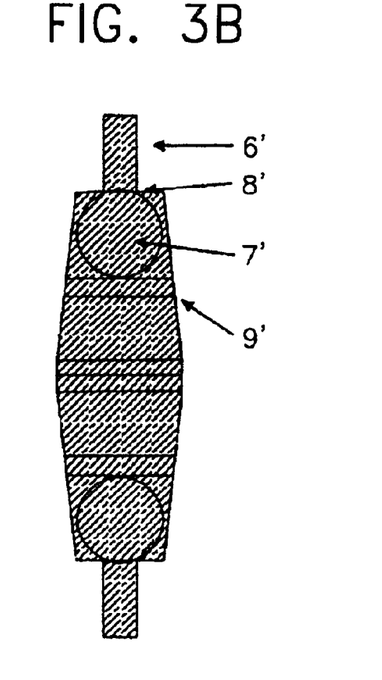
FIG. 3B is a plan view of a shaped plastic moulding.
Figure 3C:
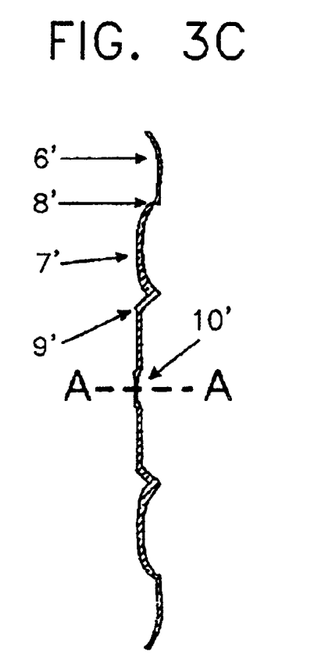
FIG. 3C is an elevational view of the plastic moulding shown in FIG. 3B.
Figure 3D:
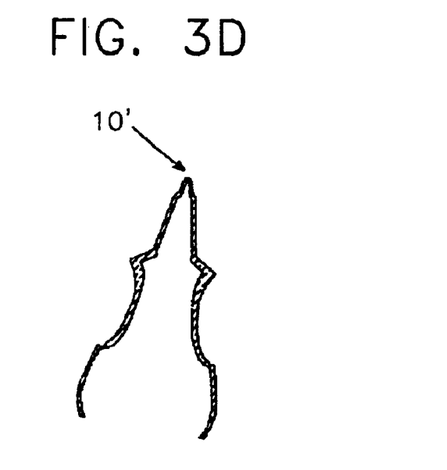
FIG. 3D is a partially folded view of the plastic moulding shown in FIGS. 3B and 3C.

FIGS. 3B and 3C illustrate a plan view and an elevation view, respectively, of a shaped plastic moulding which is used to enclose the Uniject™ device. The shaped plastic moulding is symmetrical about its central axis; the line A—A in FIG. 3C. During assembly of the injector, the shaped plastic moulding is folded about this axis A—A. An intermediate shape during the folding process is shown in FIG. 3D.

Figure 3E:
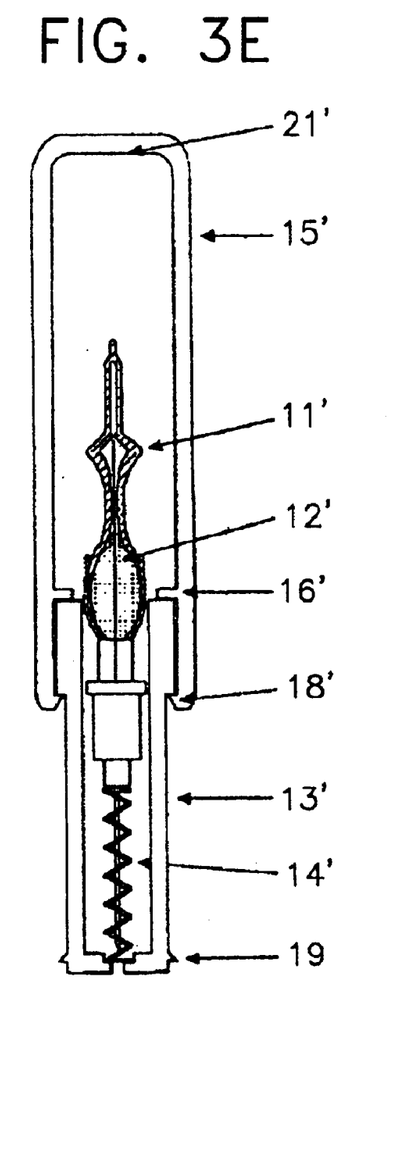
FIG. 3E is a sectional view of the plastic moulding mounted onto the blister injector contained within a cap and a barrel with a spring surrounding the syringe of the blister injector.
Figure 3F:
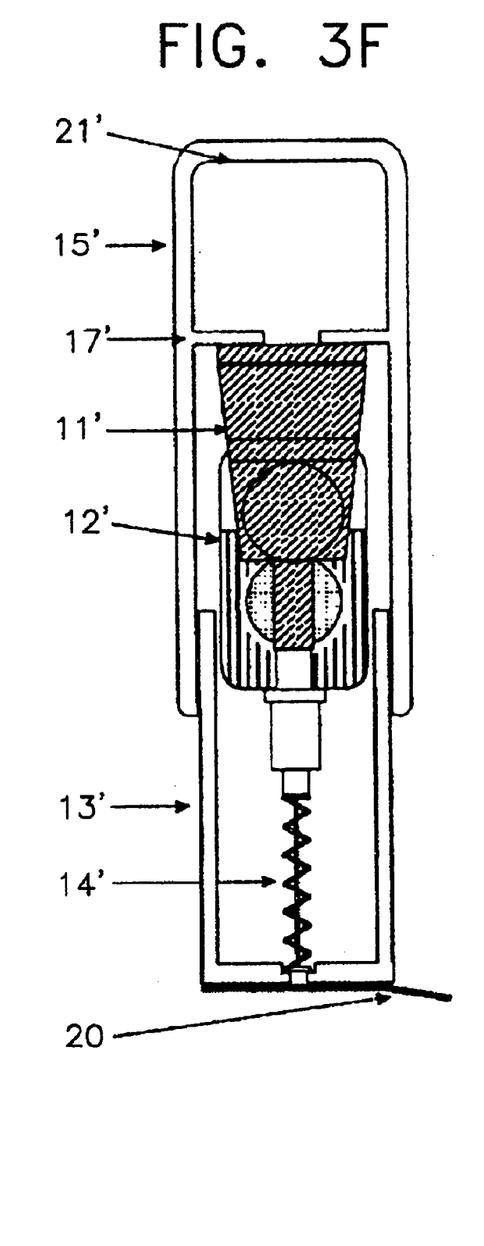
FIG. 3F is a sectional view taken along the longitudinal axis of the blister injector mounted in an injection capsule.
Figure 4A:
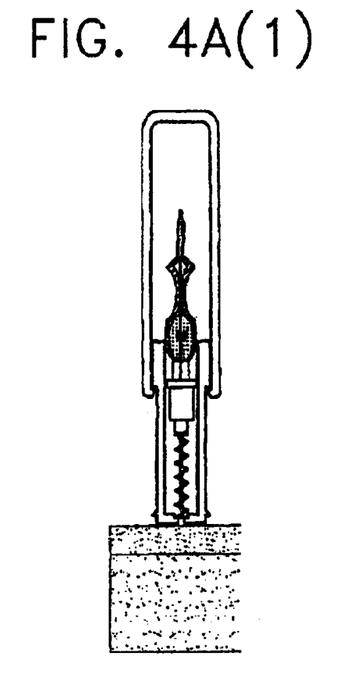
Figure 4B:
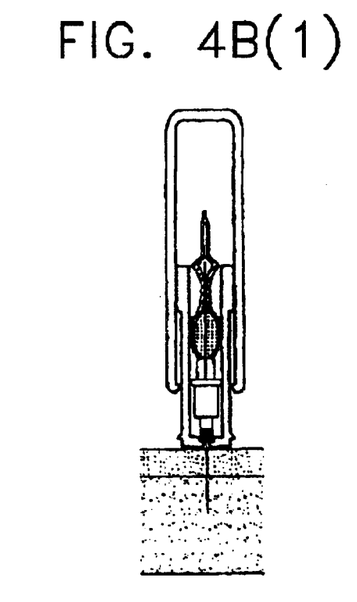
Figure 4C:
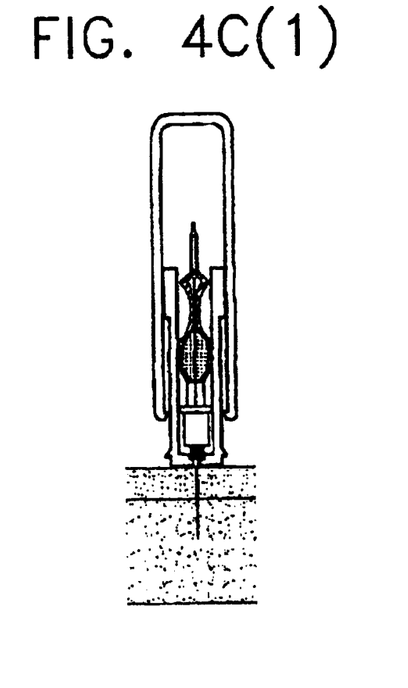
Figure 4D:
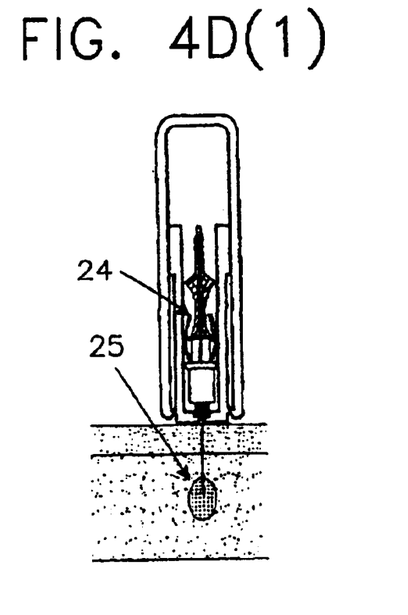
Figure 4E:
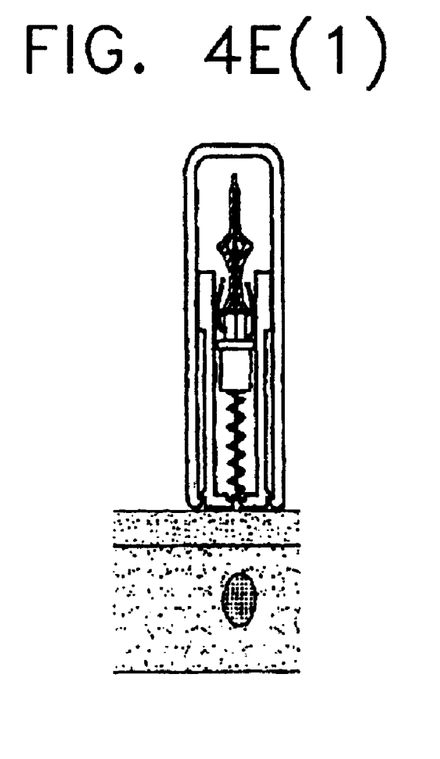

The final folded configuration is shown inside the injection capsule in FIG. 3E in which the shaped plastic moulding (11') is illustrated enclosing the Uniject™ device (12'). The moulded features of the shaped plastic moulding consist of a curved extension (6'), which is shaped to surround the blister (2') on two sides and to rest on the top of the hub (3') as shown in FIG. 3F. The curved extension (6') is attached to a dome shaped area (7'), which is similar in size but opposite in convexity to the blister. In the storage position in the device (FIGS. 3E and 3F) this dome shaped area (7') sits just above the blister in the injector device. The part of the shaped plastic moulding between the curved extension (6') and the dome (7') contains a grooved defect (8'), which weakens the structure so that it will snap at this point and not elsewhere when under a sufficient compressive force. When the shaped plastic moulding is fully folded the area of the moulding adjacent to the point of folding (10') is fused together, either with heat or adhesive to hold the moulding permanently in the fully folded position.

FIGS. 3E and 3F illustrate the final injector device assembled in the storage configuration. The whole device is oval in cross section. FIG. 3E is an elevation of the mid point section of the short axis of the oval and FIG. 3F is a mid point section of the long axis of the oval. This convention also applies to FIGS. 4A through 4E in which the device is also shown as pairs of views.

Assembly in the factory requires first that the shaped plastic moulding (11') is slid sideways over the filled Uniject™ device (12') so that the end of the curved extension (6') is located resting on the top of the hub (3') and enclosing the blister (2'). The enclosed Uniject™ is then inserted into the barrel (13') of the injector supported by a return spring (14'). The cap (15') which contains two sets of snap tabs (16') and (17') is then pushed over the barrel (13') until the first set of snap tabs (16') locates at the top of the barrel and the lock ring (18') of the cap engages with the underside of the widened part of the upper end of the barrel. At this point, the second set of snap tabs (17') also rests upon the free end of the folding (10') of the shaped plastic moulding (11') thus holding the enclosed Uniject™ snugly in place. The barrel also carries a lock ring (19') at its distal end, which will lock the cap in the closed position after use. The device is sealed against contamination and the interior maintained sterile by an adhesive transfer foil (20') having a pull tab at one end. The transfer foil (20') is applied to the distal free end of the device.

In use, the adhesive transfer foil (20') is removed from the distal free end of the device thereby transferring a layer of adhesive to the free end of the device. The distal free end of the device is pressed against the skin (22') of the patient (FIGS. 4A(1) and 4A(2)) by modest hand pressure applied to the free end (21') of the cap. The layer of adhesive serves to fix the device in position even on wet skin thus preventing slippage and damage to the patient's skin as the pressure on the cap is increase by the operator until the first set of break tabs (16') yield (FIG. 4A(2)). This suddenly frees the cap (15') to slide telescopically over the barrel (13'). This causes the second set of break tabs (17') to press on the free end of the folding (10') of the shaped plastic moulding which transmits this pressure via the shaped extension (6') to the top of the hub (3'). Downward movement of the hub compresses the spring (14') and pushes the needle into the subcutaneous tissues (23') until the plastic collar (5') on the needle bottoms out in the barrel (FIGS. 4B(1) and 4B(2)). Continued downward movement forces the collar inside the hollow hub (3') towards the blister causing the sharp hub-end of the needle to penetrate the thin plastic wall sealing the blister and giving the dose of medicament (2') access to the needle (4'). The movement of the collar inside the hollow hub stops when the collar is flush with the bottom of the hollow hub as the hub (3') in turn bottoms out in the barrel (13') (FIGS. 4C(1) and 4C(2)). The bottoming out of the hub (3') causes a sudden increase in compressive force on the curved extension (6') causing the weakened area (24') of grooved defect (8') to break (FIG. 4D(1)). This causes the shaped plastic moulding (11') to slide over the Uniject™ (12') until the dome (7') comes into register with, and presses on, the blister (2') discharging its contents of medicament through the needle (4') into the subcutaneous tissue or muscle layer (25') (FIGS. 4D(1) and 4D(2)). When the dome (7') is fully in register with the blister (2') the Uniject™ is entirely engulfed by the shaped plastic moulding and no further downward movement of the enclosed Uniject™ is possible causing an increase in pressure on the second set of break tabs (17').

The top of the barrel then also presses on the underside of the second set of break tabs (17') greatly increasing the force on them and causing them to, give way (FIGS. 4D(1) and 4D(2)). This thereby releases all downward pressure on the enclosed Uniject™. The return spring (14') then causes the enclosed Uniject™ to move suddenly into the cap as the final downward movement of the cap (15') over the barrel housing (13') causes the cap lock ring (18') to engage the barrel lock ring (19') thus securely locking the device shut and preventing any possibility of contact with the used needle (FIGS. 4E(1) and 4E(2)). Appropriate design of the device can ensure that the free end (10') of the shaped plastic moulding (11') strikes the underside of the cap giving a tactile and audible signal to the operator that the needle is fully retracted in a safe manner. If the cap (15') is made from transparent or translucent plastic, the safe retraction of the needle can be confirmed visually before the device is peeled from the patient's skin for disposal.

It is important to emphasize that the full sequence of a safe and effective injection with both devices described herein is achieved with a simple, single downward thrust. No separate operator manipulations are required to insert the needle, deliver the injection or withdraw the needle; all of which happen automatically during the single downward movement of the cap from the open to the locked position. After use the devices are locked in a safe configuration with no possibility of needlestick injury. This absence of any requirement for operator training or skill makes the present invention ideal for use by untrained personnel and even possibly for over the counter (OTC) sales to the general public.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A single use injector device for dispensing medication from a pre-filled syringe and sealing the syringe in the device after use, the pre-filled syringe including a barrel open with a flange at one end and having a needle mounted in a hub at an opposite end, a plunger slidably mounted in the barrel having a stopper at one end engaging a predetermined dose of a drug and a flange at an opposite end, the single use injector device comprising:
   a housing,
   a spring located in a lumen of the housing for engaging the hub of the barrel of the syringe,
   a cap slidably mounted on the housing for progressively moving along a longitudinal axis of the housing while the needle of the syringe is moved from an interior of the housing to an exterior of the housing and delivery of the predetermined dose of the drug and retraction of the needle into the housing after use to prevent exposure to the used needle, and
   one end of said housing being sealed with an adherent foil having a pull-tab for removal of the foil and leaving an exposed adhesive surface at the one end of the housing.

2. A single use injector device for dispensing medication from a pre-filled syringe and sealing the syringe in the device after use, the pre-filled syringe including a barrel open with a flange at one end and having a needle mounted in a hub at an opposite end, a plunger slidably mounted in the barrel having a stopper at one end engaging a predetermined dose of a drug and a flange at an opposite end, the single use injector device comprising:
   a housing,
   a spring located in a lumen of the housing for engaging the hub of the barrel of the syringe, and
   a cap slidably mounted on the housing for progressively moving along a longitudinal axis of the housing while the needle of the syringe is moved from an interior of the housing to an exterior of the housing and delivery of the predetermined dose of the drug and retraction of the needle into the housing after use to prevent exposure to the used needle,
   said cap including three sets of break tabs, a first set of said three sets of break tabs engaging one end of the housing prior to movement of the syringe in the housing, a second set of said three sets of break tabs engaging the flange of the barrel of the syringe after the first set of break tabs is broken by movement of the cap, a third set of said three sets of break tabs engaging the flange of the plunger of the syringe after the first set and the second set of break tabs are broken, the third set of said three sets of break tabs being broken upon movement of the cap along the barrel after breaking of the first and second sets of break tabs,
   the first set of break tabs projecting into the interior of the cap less than the second and third sets of break tabs and the second set of break tabs projecting into the interior of the cap less than the third set of break tabs.

3. The single use injector device as claimed in claim 2, wherein the spring retracts the needle into the housing and moves the plunger and the barrel of the syringe up into the cap after the third set of break tabs is broken.

4. The single use injector device as claimed in claim 3, wherein a locking ring of the cap engages a locking ring of the housing to lock the cap and housing together after extension and retraction of the needle from the housing to prevent exposure to the used needle.

5. A single use injector comprising:
   a container for medication;
   an expulsion device for expelling the medication from the container;
   a needle for delivering the expelled medication through the skin of a patient;
   an operating mechanism designed to apply hand pressure to push the needle through the skin and to operate the expulsion device;
   a spring-action mechanism to withdraw the needle into the operation mechanism after use; and
   a detent releasing in response to hand pressure greater than a predetermined value so that the operating mechanism is caused to operate in two stages:
   a) a first stage, before release of the detent, in which the application of pressure pushes the needle through the skin, and
   b) a second stage, after release of the detent, in which continued application of pressure operates the expulsion device.

6. The injector according to claim 5, further comprising a final detent which releases in response to the hand pressure greater than a second predetermined value, greater than the first predetermined value, to release the spring-action mechanism so that the needle is withdrawn.

7. The injector according to claim 6, further comprising an initial detent which releases in response to hand pressure being greater than an initial value thereby allowing the needle to be pushed through the skin of the patient.

8. The injector according to claim 7, wherein the operating mechanism includes a housing which encloses the needle before the initial detent is released and after the final detent is released.

9. The injector according to claim 8, wherein the container includes a barrel and a plunger slides in the barrel to expel the medication, the detent acting directly between the barrel and the operating mechanism to push the needle through the skin of the patient, and the operating mechanism is effective, after release of the detent, to operate the plunger to expel the medication.

10. A single use injector device for dispensing medication from a pre-filled syringe and sealing the syringe in the device after use, the pre-filled syringe including a blister having a predetermined dose of a drug, a hollow hub, a collar and a needle mounted on the collar, the single use injector comprising:

a shaped moulding for engaging the blister,
a barrel,
a spring located in the barrel, and
a cap slidably mounted on the barrel progressively moving along a longitudinal axis of the barrel while the needle of the syringe is moved from an interior of the barrel to an exterior of the barrel and delivery of the predetermined dose of the drug and retraction of the needle into the barrel after use to prevent exposure to the used needle.

11. The single use injector device as claimed in claim 10, wherein movement of the cap with respect to the barrel causes one end of the needle to puncture a patient's skin and an opposite end of the needle punctures the blister containing the drug by extension of the needle through the hollow hub.

12. The single use injector device as claimed in claim 10, wherein one end of said barrel is sealed with an adherent foil having a pull-tab for removal of the foil and leaving an exposed adhesive surface at the one end of the barrel.

13. The single use injector device as claimed in claim 10, wherein said cap includes two sets of break tabs.

14. The single use injector device as claimed in claim 13, wherein a first set of said two sets of break tabs engages one end of said barrel prior to movement of the syringe in the barrel.

15. The single use injector device as claimed in claim 14, wherein a second set of said two sets of break tabs engages an end of said syringe opposite to the needle and moves a dome shaped area of the shaped moulding to squeeze said blister after breakage of the first set of break tabs.

16. The single use injector device as claimed in claim 15, wherein continued movement of the cap with respect to the barrel after breakage of the first set of tabs causes breakage of the second set of tabs and movement of the syringe into the cap and retraction of the needle by a bias force of the spring.

17. The single use injector device as claimed in claim 10, wherein the moulding includes two curved extensions.

18. The single use injector device as claimed in claim 17, wherein the curved extensions each include a grooved defect.

19. The single use injector device as claimed in claim 11, wherein the moulding is folded in half.

* * * * *